United States Patent [19]

Carret et al.

[11] Patent Number: 5,458,650
[45] Date of Patent: Oct. 17, 1995

[54] ELASTICALLY DEFORMABLE COTYLOIDAL PROSTHESIS

[75] Inventors: Jean-Paul Carret, Saint-Fons;
Paul-Louis Fischer, Tassin;
Jean-Christophe Chatelet;
Michel-Henri Fessy, both of Lyons;
Michel Bonnin, Sainte-Foy-Les Lyon;
Laurent Nove-Josserand; Jacques Bejui, both of Lyons; Olivier Galland, Meylan, all of France

[73] Assignee: Tornier S.A., Saint-Ismier, France

[21] Appl. No.: 207,048

[22] Filed: Mar. 8, 1994

[30] Foreign Application Priority Data

Mar. 30, 1993 [FR] France .................... 93 03949

[51] Int. Cl.$^6$ ...................................... A61F 2/34
[52] U.S. Cl. ............................ 623/22; 623/18
[58] Field of Search .................... 623/16, 18, 19, 623/20, 22, 23

[56] References Cited

U.S. PATENT DOCUMENTS

| | | | |
|---|---|---|---|
| 4,596,580 | 6/1986 | Weill | 623/22 |
| 4,650,491 | 3/1987 | Parchinski | 623/22 |
| 4,828,565 | 5/1989 | Duthoit et al. | 623/22 |
| 4,871,368 | 10/1989 | Wagner | 623/22 |
| 4,904,265 | 2/1990 | MacCollum et al. | 623/22 |
| 4,936,861 | 6/1990 | Muller et al. | 623/22 |
| 5,041,140 | 8/1991 | Teinturier | 623/22 |
| 5,092,897 | 3/1992 | Forte | 623/22 |
| 5,108,448 | 4/1992 | Gautier | |

FOREIGN PATENT DOCUMENTS

| | | |
|---|---|---|
| 0091315 | 10/1983 | European Pat. Off. |
| 0482320 | 4/1992 | European Pat. Off. |
| 3916891 | 12/1989 | Germany |

*Primary Examiner*—David Isabella
*Attorney, Agent, or Firm*—Dowell & Dowell

[57] ABSTRACT

An elastically deformable cotyloidal prosthesis including a hollow hemispherical cap which includes an outer surface including portions which are deformable while the inner surface thereof is rigid and which further includes a plastic insert having a hemispherical cavity which communicates with an outer beveled edge defining a cylindrical opening thereto. The insert is rotatably adjustable and securable relative to the inner surface of the cap.

15 Claims, 1 Drawing Sheet

ELASTICALLY DEFORMABLE COTYLOIDAL PROSTHESIS

BACKGROUND OF THE INVENTION

1. Field of the Invention

The present invention relates to an elastically deformable cotyloidal prosthesis comprising an acetabulum or a hollow hemispherical cap made of metal, composite or the like, which is stabilized in the bone by screws and a plastic insert which clips inside the cap.

2. History of the Related Art

Cotyloidal prostheses of this type are known, in which the outer wall of the hollow hemispherical cap has a series of expansion slots therein. These slots are made in the direction of the center of the cap and at least one of them opens out in a hole, eccentric or not, thus defining a part of cap in a plurality of segments. Such segmentation gives a certain suppleness to the hollow hemispherical cap and facilitates positioning thereof in the human acetabulum.

Such cotyloidal prostheses present certain drawbacks concerning the reduction of the inner diameter of the hollow hemispherical cap during positioning inside the cavity of the human acetabulum. In fact, the expansion slots give a certain suppleness to the cap, but reduce the inner diameter thereof, which renders difficult, and even impossible, in certain cases, the positioning of the plastic insert.

It is a more particular object of the present invention to overcome these drawbacks.

SUMMARY OF THE INVENTION

The cotyloidal prosthesis according to the invention comprises an acetabulum or a hollow hemispherical cap comprising means for its outer face to deform elastically, while its inner wall remains rigid and undeformable.

Said means consist of a certain number of slots which are made in the thickness of the cap so as to open out on the outer face and on the edge thereof, whilst at least two of the slots have, perpendicularly to one of their open ends, a groove extending towards the outside of the cap to constitute two supple wing elements.

In addition, the cotyloidal prosthesis comprises an insert of plastic material which is provided with a cavity centered on the axis of symmetry of the prosthesis, and an inner bevel inclined by an angle α with respect to the axis of symmetry in order to define an inner cylinder portion.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
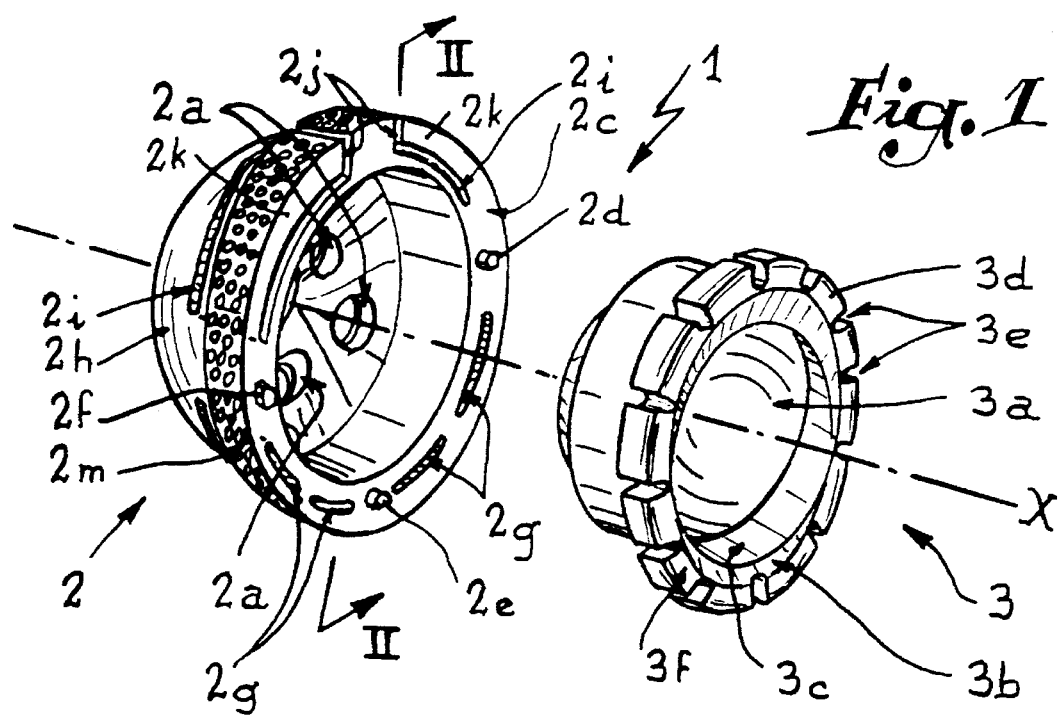
FIG. 1 is a view in perspective illustrating the cotyloidal prosthesis according to the invention before assembly and more particularly the hollow hemispherical cap and the plastic insert.
Figure 2:
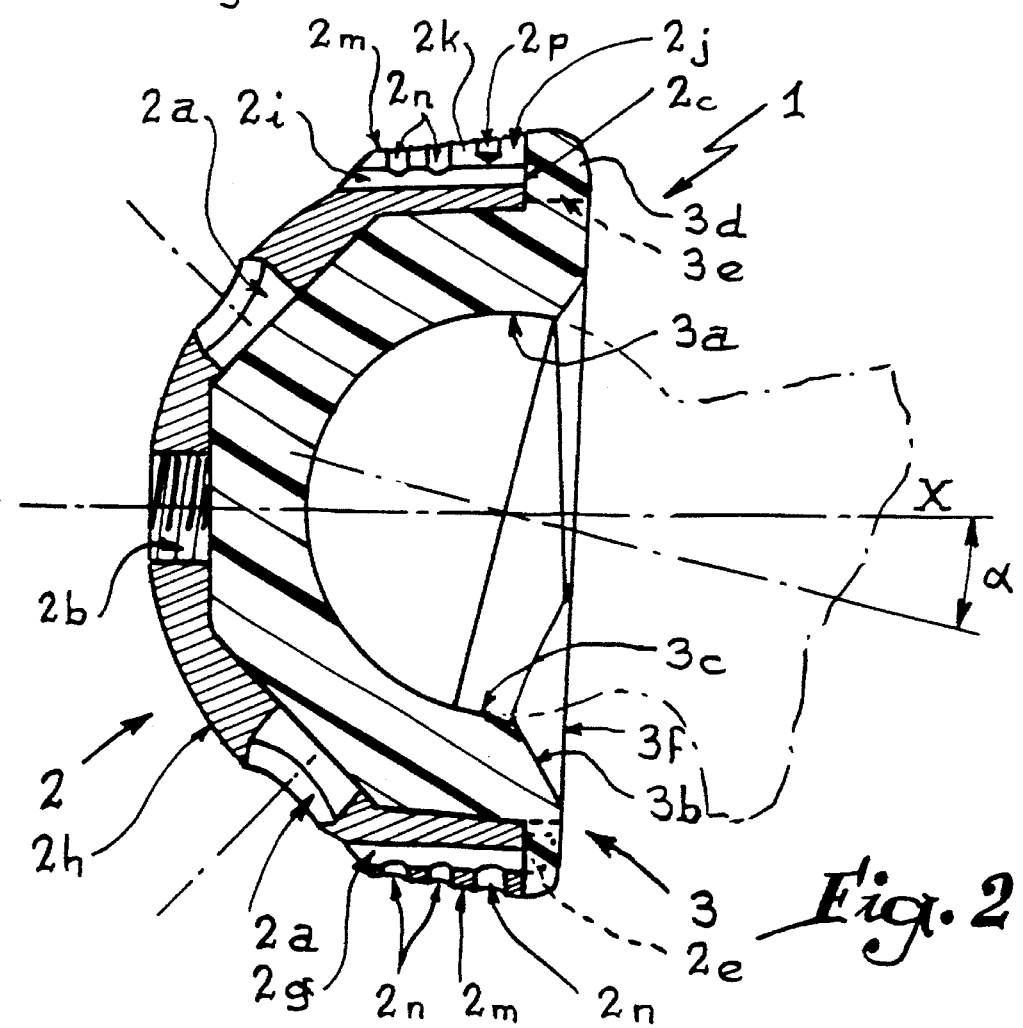
FIG. 2 is a section along II—II (FIG. 1) showing the cotyloidal prosthesis after assembly of the plastic insert in the hollow hemispherical cap.

Referring now to the drawings, FIGS. 1 and 2 show a cotyloidal prosthesis 1 comprising an acetabulum or cap 2 made of titanium or the like, and an insert 3 of plastic material such as polyethylene.

The hemispherical cap 2 comprises, on part of its outer face 2h, a plurality of holes 2a disposed along different radii and allowing the passage of screws. The center of the cap 2 is pierced with a tapped opening hole 2b allowing fixation of an ancillary element for the introduction of said cap in the human acetabulum.

The circular edge 2c of the cap 2 is provided with three studs 2d, 2e and 2f which are equally spaced over half of the periphery of the edge 2c. In fact, the studs 2d and 2f are aligned along one of the axes of symmetry of the cap 2, while the stud 2e is oriented along the other axis of symmetry, i.e. at 90° from the other two studs.

On the edge 2c and between studs 2d and 2e and studs 2e and 2f are slots 2g which open on the outer face 2h of the cap 2. Similarly, opposite the slots 2g and between the studs 2d and 2f are two slots 2i which open out on the outer face 2h of the cap. The free ends of the slots 2i which are located opposite, extend perpendicularly in a groove 2j which extends outwardly of the cap 2 so as to constitute two supple, elastic wing elements 2k. It will be noted that, on the outer face 2h of the cap 2, the slots 2g and 2i open beyond the first row of holes 2a.

Similarly, between the edge 2c and the first row of holes 2a, there is a zone 2m which allows the osseous callus to catch on the outer face 2h of the cap. This zone 2m is constituted by a series of holes 2n which open in the slots 2g and 2i and a series of non-opening holes 2p which give a particular aspect to the surface. The holes 2n which open in the slots 2g and 2i make it possible to create a system of chambers and channels on the periphery of the outer face 2h of the cap 2 to ensure a better take-up and vascularization of the osseous callus. This particular take-up of the osseous callus allows a secondary stability of the cotyloidal prosthesis 1 of biological type and not mechanical type.

In the plastic insert 3 includes a cavity 3a which presents the same axis of symmetry X of the cotyloidal prosthesis 1 (FIG. 2). Cavity 3a comprises an inner bevel 3b which is inclined by an angle α of about 15° with respect to the axis X of the prosthesis 1. The inclination of the bevel 3b inside the cavity 3a defines a portion of cylinder 3c which makes it possible to avoid certain types of dislocation. In fact, when the human or artificial cephalic ball is introduced in the cavity 3a of the insert 3 as shown by dotted lines in FIG. 2, it sometimes happens that, under too great an effort, the cephalic ball is dislodged from the cotyloidal prosthesis. The 3c of the insert 3 is thus provided to avoid this type of stress and trouble for the patient.

The insert 3 is provided with a flange 3d which has on its periphery a series of notches 3e which cooperate with the studs 2d, 2e and 2f of the cap when the insert 3 is introduced therein.

The outer flange 3d has a variable thickness, thus forming an inclined outer face 3f in order that, by simple rotation of the insert 3 in the cap 2, the plane of the face may be changed depending on each pathological case.

It is understood that the outer diameter of the hemispherical cap 2 may vary during introduction thereof in the human cavity in order to avoid certain stresses which are awkward for the patient, without deforming its inner diameter. The non-deformation of the inner diameter of the hollow hemispherical cap 2 allows a perfect, easy positioning of the insert 3.

It must, moreover, be understood that the foregoing description has been given by way of example and that it in no way limits the domain of the invention which would not be exceeded by replacing the details of execution described by any other equivalents.

What is claimed is:

1. A cotyloidal prothesis mounting to a cephalic ball comprising; a hollow hemispherical metallic material cap having inner and outer surface portions which are connected along a circular edge, said inner surface portion being rigid, a plastic insert seated within said cap in contact with said inner surface portion, a plurality of spaced slots formed in said cap between said inner and outer surface portions and each slot opening through each of said outer surface portion and said circular edge, at least two of said slots communicating with open grooves extending from said slots to the outer surface portion of said cap thereby defining at least two yieldable wing elements, a plurality of spaced holes extending through said inner and outer surface portions of said cap portion through which fastening elements may be received, and said holes being spaced from said slots.

2. The prothesis of claim 1 in which said cap includes an axis of symmetry extending through a center portion thereof, said plastic insert including a cavity generally centered on said axis of symmetry and an inner bevel into said cavity which defines a cylindrical portion communicating with said cavity but disposed at an angle $\alpha$ with respect to said axis of symmetry.

3. The prothesis of claim 2 wherein said plastic insert further includes a generally angular flange having a plurality of spaced notches therein, said flange engaging said edge of said cap, said flange varying in thickness and defining an outer face oriented along a common plane, whereby the change of thickness of said flange causes the plane of the outer face to change upon rotation of said insert relative to said cap.

4. The prosthesis of claim 3 wherein a plurality of studs extend from said circular edge of said cap, said studs being engageable within said notches of said flange.

5. The prosthesis of claim 4 wherein said angle a is equal to approximately 15 degrees with respect to said axis of symmetry of said cap.

6. The prosthesis of claim 2 including three studs extending from said circular edge of said cap, two of said studs being aligned parallel with said axis of symmetry of said cap and the third of said studs extending at an angle $\alpha$ with respect to said axis of symmetry of said cap.

7. The prothesis of claim 6 including at least one slot between each of said studs along said circular edge, and said yieldable wing elements being positioned between two generally oppositely oriented studs.

8. The prosthesis of claim 2 wherein said outer face portion of said cap includes a zone for the construction of an osseous callus included between said edge and said spaced holes.

9. The prosthesis of claim 8 wherein said zone includes a first number of holes which communicate with said slots and said outer surface portion of said cap.

10. The prosthesis of claim 9 in which said zone further includes a second number of holes which extend from said outer surface portion of said cap and terminate in spaced relationship with respect to said slots.

11. A cotyloidal prosthesis for mounting to a cephalic ball comprising; a hollow hemispherical metallic material cap having inner and outer surface portions which are connected along a circular edge, said inner surface portion being rigid, a plastic inserted seated within said inner portion, a plurality of spaced slots formed in said cap between said inner and outer surface portions and open through said outer surface portion and said circular edge, at least two of said slots communicating with open grooves extending from said slots to the outer surface portion of said cap to thereby define at least two yieldable wing elements, said outer surface portion including a zone for the ingrowth of an osseous callus adjacent said edge.

12. The prosthesis of claim 11 wherein said zone includes a first number of holes which communicate with said slots and said outer surface portion of said cap, and a second number of holes which extend from said outer surface portion of said cap into spaced relationship with respect to said slots.

13. The prosthesis of claim 12 wherein said edge includes a plurality of studs which extend therefrom, said plastic insert including an annular flange having a plurality of spaced notches therein in which said studs are selectively receivable to attach said insert to said cap.

14. The prosthesis of claim 13 wherein said flange of said insert is varying in thickness and includes an outer face disposed along a plane, said plane being variable by rotating said insert relative to said cap.

15. The prosthesis of claim 14 wherein said cap includes a plurality of holes opening therethrough through which fastening elements may be inserted, said holes being spaced from said zone of said cap.

* * * * *